United States Patent [19]

Gregson et al.

[11] 4,267,320

[45] May 12, 1981

[54] CEPHALOSPORIN ANTIBIOTICS

[75] Inventors: Michael Gregson, Middlesex; Richard B. Sykes, Chalfont St. Giles, both of England

[73] Assignee: Glaxo Laboratories Limited, England

[21] Appl. No.: 61,260

[22] Filed: Jul. 27, 1979

Related U.S. Application Data

[63] Continuation of Ser. No. 921,120, Jun. 30, 1978, abandoned, which is a continuation of Ser. No. 768,720, Feb. 15, 1977, abandoned.

[30] Foreign Application Priority Data

Feb. 16, 1976 [GB] United Kingdom ............... 6009/76
Jun. 30, 1976 [GB] United Kingdom ............. 27301/76
Jun. 30, 1976 [GB] United Kingdom ............. 27302/76

[51] Int. Cl.³ .......................................... C07D 501/34
[52] U.S. Cl. ...................................... 544/22; 424/246
[58] Field of Search ............................................. 544/22

[56] References Cited

U.S. PATENT DOCUMENTS

| | | | |
|---|---|---|---|
| 3,819,601 | 6/1974 | Rosati | 424/246 |
| 3,870,713 | 3/1975 | Hamanaka | 424/246 |
| 3,962,227 | 6/1976 | Chauvette | 544/22 |
| 3,974,153 | 8/1976 | Cook et al. | 424/246 |

FOREIGN PATENT DOCUMENTS 2405877 2/1974 Fed. Rep. of Germany.
1310642 3/1973 United Kingdom.

Primary Examiner—Paul M. Coughlan, Jr.
Attorney, Agent, or Firm—Bacon & Thomas

[57] ABSTRACT

The invention provides novel antibiotic cefuroxime esters of the formula

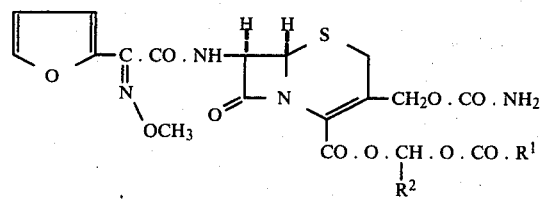

(wherein $R^1$ is a primary or secondary alkyl group containing 1 to 4 carbon atoms and $R^2$ is a primary or secondary alkyl group containing 1 to 6 carbon atoms provided that at least one of the groups $R^1$ and $R^2$ is methyl). These compounds are useful as orally administrable broad spectrum antibiotics.

11 Claims, No Drawings

CEPHALOSPORIN ANTIBIOTICS

This is a continuation of application Ser. No. 921,120, filed June 30, 1978, now abandoned, which in turn is a continuation of application Ser. No. 768,720, filed Feb. 15, 1977, now abandoned.

This invention is concerned with improvements in or relating to cephalosporin antibiotics. More particularly the invention is concerned with biologically acceptable ester derivatives of (6R,7R)-3-carbamoyloxymethyl-7-[(Z)-2-(fur-2-yl)-2-methoxyiminoacetamido]ceph-3-em-4-carboxylic acid (ie the syn isomer), which has the approved name "cefuroxime".

Cefuroxime, as disclosed in British Pat. No. 1,453,049 is a valuable broad spectrum antibiotic characterised by high activity against a wide range of gram-positive and gram-negative microorganisms, this property being enhanced by the very high stability of the compound to $\beta$-lactamases produced by a range of gram-negative microorganisms. Additionally the compound is stable in the body owing to its resistance to the action of mammalian esterases, and gives high serum levels following parenteral administration (e.g. in the form of the sodium salt) to human and animal subjects, while exhibiting low serum binding.

Cefuroxime and its salts, for example alkali metal salts such as the sodium salt, are principally of value as injectable antibiotics since they are poorly absorbed from the gastro-intestinal tract and are therefore present in sera and urine only in low concentrations after oral administration. We have accordingly conducted extensive studies into the possible activity upon oral administration of various derivatives of cefuroxime, since the development of derivatives which are absorbed through the gastro-intestinal tract and exhibit good antibacterial activity following oral administration would extend still further the valuable therapeutic potential of cefuroxime.

It is known from the literature pertaining to $\beta$-lactam antibiotics that the effect upon oral administration of penicillin antibiotics such as ampicillin can be improved by converting the carboxy group at the 3-position of the penam nucleus to certain esterified carboxy groups; there have also been some proposals that the activity upon oral administration of certain cephalosporin antibiotics may be enhanced by esterification in similar manner. It is believed that the presence of an appropriate esterifying group enhances absorption of the compound from the gastro-intestinal tract, whereupon the esterifying group is hydrolysed by enzymes present in, for example, serum and body tissues to yield the antibiotically active parent acid. It will be appreciated that the precise nature of the esterifying group is critical since it is necessary that the ester be sufficiently stable to allow the ester to reach the site of absorption without undergoing significant degradation, e.g. in the stomach, while on the other hand the ester must be sufficiently susceptible to esterase hydrolysis so that the antibiotically active parent acid is liberated within a short time of the ester being absorbed.

The selection of a particular esterifying group to enhance the effect upon oral administration of a $\beta$-lactam antibiotic will also be influenced by the specific $\beta$-lactam compound chosen. Thus, for example, esterifying groups which have been found effective in improving the activity of orally administered penicillin antibiotics do not necessarily convey similar advantages to antibiotics of the cephalosporin series. An example which may be cited here is the case of pivaloyloxymethyl esters. Thus, the pivaloyloxymethyl ester of, for example, ampicillin is known to improve the oral absorption of ampicillin. The pivaloyloxymethyl ester of cefuroxime, on the other hand, exhibits little effect upon oral administration, possibly because the ester is not absorbed from the gastro-intestinal tract or alternatively is substantially resistant to esterase hydrolysis so that the antibiotically active acid is not liberated to any significant extent following absorption.

We have now found that esters of cefuroxime, which may be represented by the formula

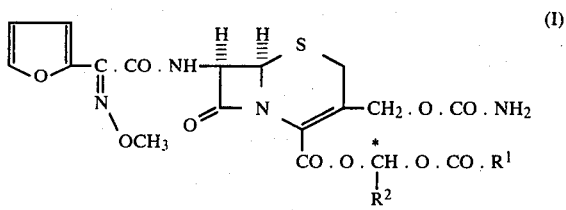

(wherein $R^1$ is a primary or secondary alkyl group containing 1 to 4 carbon atoms and $R^2$ is a primary or secondary alkyl group containing 1 to 6 carbon atoms provided that at least one of the groups $R^1$ and $R^2$ is methyl, and the asterisk denotes an asymmetric carbon atom) possess properties which render these compounds of significant potential value as orally administrable antibiotics. The individual diastereoisomers, as well as mixtures thereof, are embraced by the invention.

Examples of compounds of formula I include those wherein $R^1$ is a methyl group and $R^2$ is an alkyl group containing 2 to 4 carbon atoms and those wherein $R^2$ is a methyl group and $R^1$ is a primary or secondary alkyl group containing 1 to 4 carbon atoms.

The esters (I) possess reasonable stability as evidenced by the fact that they exhibit low antibacterial activity in vitro compared to cefuroxime (this indicates that a high proportion of ester remains unchanged throughout the in vitro tests and so confirms the stability of the esters). The esters are, on the other hand, extremely susceptible to esterase hydrolysis leading to formation of cefuroxime, as evidenced by in vitro tests employing esterases derived from rat liver, human liver and human serum.

In vivo testing in rats confirms that oral administration of the esters (I) leads to significantly greater absorption of cefuroxime, as evidenced by higher serum levels and increased urinary recovery, than does oral administration of cefuroxime itself.

Of the compounds of formula (I) the following have been shown to provide particularly good absorption of cefuroxime:

1-acetoxyethyl (6R,7R)-3-carbamoyloxymethyl-7-[(Z)-2-(fur-2-yl)-2-methoxyiminoacetamido]ceph-3-em-4-carboxylate;

1-propionyloxyethyl (6R,7R)-3-carbamoyloxymethyl-7-[(Z)-2-(fur-2-yl)-2-methoxyiminoacetamido]ceph-3-em-4-carboxylate;

1-butyryloxyethyl (6R,7R)-3-carbamoyloxymethyl-7-[(Z)-2-(fur-2-yl)-2-methoxyiminoacetamido]ceph-3-em-4-carboxylate;

1-isovaleryloxyethyl (6R,7R)-3-carbamoyloxymethyl-7-[(Z)-2-(fur-2-yl)-2-methoxyiminoacetamido]ceph-3-em-4-carboxylate;

1-acetoxyheptyl (6R,7R)-3-carbamoyloxymethyl-7-[(Z)-2-(fur-2-yl)-2-methoxyiminoacetamido]ceph-3-em-4-carboxylate;

1-acetoxybutyl (6R,7R)-3-carbamoyloxymethyl-7-[(Z)-2-(fur-2-yl)-2-methoxyiminoacetamido]ceph-3-em-4-carboxylate;

1-acetoxypropyl (6R,7R)-3-carbamoyloxymethyl-7-[(Z)-2-(fur-2-yl)-2-methoxyiminoacetamido]ceph-3-em-4-carboxylate.

The first compound mentioned above is particularly preferred, since it provides especially high absorption of cefuroxime as shown by in vivo testing in mice, rats and dogs.

The compounds (I) may be prepared in conventional manner, for example by reacting cefuroxime or a salt thereof (e.g. an alkali metal salt such as the sodium or potassium salt or an onium salt, e.g. an ammonium salt for example a quaternary ammonium salt) with a haloester of formula

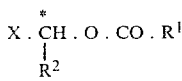
(II)

(where $R^1$, $R^2$ and the asterisk have the above-defined meanings and X is halogen such as chlorine, bromine or iodine). The reaction is conveniently effected in solution in an inert organic solvent (e.g. an N,N-disubstituted amide such as N,N-dimethylformamide or N,N-dimethylacetamide, a ketone such as acetone, a sulphoxide such as dimethylsulphoxide, a nitrile such as acetonitrile, or hexamethylphosphoric triamide) at a temperature in the range −50° to +150° C., e.g. −10° to +50° C., conveniently between 0° C. and room temperature. When a cefuroxime salt, for example, the potassium salt, is employed as starting material and the reaction is effected in a nitrile solvent, a crown ether such as 18-crown-6 may, if desired, be employed. When cefuroxime acid is employed as starting material it may be advantageous to effect the reaction in the presence of a base, e.g. a weak inorganic base such as sodium carbonate or potassium carbonate; it is convenient to add the base to the cefuroxime-containing reaction system prior to addition of the haloester (II). The use of potassium carbonate as base in conjunction with a compound (II) in which X is bromine or iodine has been found advantageous in that under these conditions the formation of a ceph-2-em ester product is kept to a minimum. It is convenient to employ substantially equivalent amounts of cefuroxime and base, e.g. about 0.5 moles of a diacidic base such as potassium carbonate per mole of cefuroxime. The haloester (II) is conveniently employed in slight excess, e.g. in an amount of 1-1.5 moles per mole of cefuroxime.

The course of the reaction may readily be monitored by t.l.c., since the process involves conversion of a polar acid or salt starting material to a neutral ester product.

The esters (I) may also be prepared by acylation of a compound of formula:

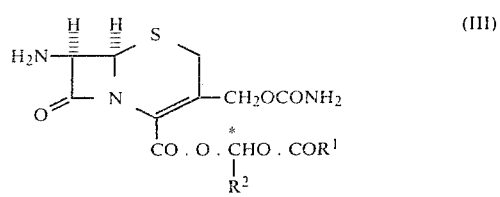
(III)

(wherein $R^1$ and $R^2$ are as hereinbefore defined) or an acid addition salt or N-silyl derivative thereof, using (Z)-2-(fur-2-yl)-2-methoxyiminoacetic acid or a reactive derivative thereof, for example in the manner disclosed in the aforementioned British Pat. No. 453,049.

The compounds of formula (I) may conveniently be prepared by acylating a compound of formula (III) with an acylating agent comprising an acid halide, particularly an acid chloride or bromide of the said acid. Such acylation may be effected at temperatures of from −50° to +50° C., preferably −20° to +30° C. The acylation may be effected in aqueous or non-aqueous media.

Acylation with an acid halide may be effected in the presence of an acid binding agent (e.g. a tertiary amine such as triethylamine or dimethylaniline, an inorganic base such as calcium carbonate or sodium bicarbonate, or an oxirane, preferably a lower-1,2-alkylene oxide such as ethylene oxide or propylene oxide) which serves to bind hydrogen halide liberated in the acylation reaction.

The free acid may itself be used as the acylating agent. Such acylations are desirably conducted in the presence of, for example, a carbodiimide such as N,N′-dicyclohexylcarbodiimide; a carbonyl compound such as carbonyldiimidazole; or an isoxazolinium salt such as N-ethyl-5-phenylisoxazolinium-3′-sulphonate or n-t-butyl-5-methylisoxazolinium perchlorate. The condensation reaction is desirably effected in an anhydrous reaction medium, e.g. methylene chloride, dimethylformamide or acetonitrile.

Acylation may also be effected with other amide-forming derivatives of the free acid such as, for example, a symmetrical anhydride or a mixed anhydride, e.g. with pivalic acid or formed with a haloformate such as a lower alkyl haloformate. The mixed or symmetrical anhydrides may be generated in situ. Thus, for example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluene-sulphonic acid).

The above-described starting materials of formula (III) may be prepared in conventional manner, for example, using the techniques described in U.S. Pat. No. 3,905,963 and British Pat. Nos. 1,041,985 and 1,350,772.

If the desired ester product is significantly contaminated by the corresponding ceph-2-em isomer the product may be oxidised (e.g. by treatment with a peracid such as metaperiodic acid, peracetic acid, monoperphthalic acid or m-chloroperbenzoic acid or with t-butyl hypochlorite in the presence of a weak base such as pyridine) to give the ceph-3-em 1-oxide ester, which may then be reduced (e.g. by treatment with acetyl chloride and potassium iodide) to yield substantially pure ceph-3-em ester.

The individual diastereoisomers may be isolated by recrystallisation from the isomeric mixture.

The esters of formula I may be formulated as compositions for oral administration in conventional manner, with the aid of any necessary pharmaceutical carriers or excipients. The compositions are conveniently prepared as tablets, capsules or sachets, advantageously in unit dose form, and may contain conventional excipients such as binding agents, fillers, lubricants, disintegrants and wetting agents. Tablets may be coated in conventional manner. The active compounds may further be formulated in rectal compositions such as suppositories or retention enemas.

The compositions may contain from 0.1% upwards, e.g. 0.1–99%, conveniently from 10–60% of the active ingredient (I), depending on the method of administration. Compositions in dosage unit form conveniently contain 50–500 mg of the active ingredient (calculated as cefuroxime). Doses employed for adult human treatment will typically be in the range 500–5000 mg per day, e.g. 1500 mg per day, (calculated as cefuroxime), although the precise dose will depend on, inter alia, the frequency of administration.

The following Examples illustrate the invention. All temperatures are in °C. The melting points were determined by the capillary method and are uncorrected. Those prefixed ($M_y^x$) where x is the rate of heating (in °C. per minute) and y is the insertion temperature were measured in a Mettler apparatus. In Example 5 the potassium carbonate employed was dried at 120° in vacuo and finely ground. The N,N-dimethylformamide employed was dried and purified by passage through acidic alumina.

HPLC stands for "high pressure liquid chromatography". Detection was achieved by ultraviolet light at 276 nm. Relative peak areas were measured at this wavelength. (The $\lambda_{max}$ of the desired compound occurs at 276 to 277 nm).

The n.m.r. spectra figures for the products of the Examples 1 to 7 given in Table 1 hereinafter indicate that the compounds are obtained as approximately 1:1 mixtures of the R and S isomers.

PREPARATION 1

(R,S) 1-Bromoethyl propionate

Acetaldehyde (1.7 ml, 1.34 g, 30.5 mmole) was added dropwise with stirring to propionyl bromide (3.18 g, 23.2 mmole) (0°–5° C.). The mixture was allowed to warm up to room temperature (ca 20°) over 1 hour. The product was distilled to give the title ester (2.7 g) as a liquid b.p. 41° to 50°/15 mm which was characterised by its nmr (CDCl$_3$) and infrared (CHBr$_3$) spectra.

PREPARATION 2

(R,S) 1-Bromoethyl n-butyrate

Acetaldehyde (2 ml) was added dropwise with stirring to n-butyryl bromide (2.09 g, 13.8 mmole) at 0°–10° C. After the initial reaction the mixture was stored at ca 4° for 2 days. The product was distilled to give the title ester (1.87 g) as a liquid b.p. 63° to 65°/14 mm which was characterised by its nmr (CDCl$_3$) and infrared (CHBr$_3$) spectra.

PREPARATION 3

(R,S) 1-Bromoethyl 3-methylbutyrate

Acetaldehyde (2.3 ml, 1.8 g, 41 mmole) was added dropwise with stirring to 3-methylbutyryl bromide (5.33 g, 32 mmole) at 0° C. The mixture was allowed to warm up to room temperature (ca. 20° C.) over half an hour.

The title ester was isolated in two fractions (2.99 g and 1.64 g) by distillation; b.p's 60° to 70°/25 mm and 70° to 75°/25 mm respectively.

Both fractions were characterised by their nmr (CDCl$_3$) spectra. The second fraction was the purer by nmr.

PREPARATION 4

(R,S) 1-Bromo-n-butyl acetate

To cooled (ca 0°) acetyl bromide (1.49 ml, 20 mmole) was added n-butyraldehyde (1.76 ml, 20 mmole). The reaction mixture was allowed to warm up to room temperature over 1 hour to give a pale brown solution. This was distilled in vacuo to give two fractions:
(i) bp 60° to 70°/27 mm (0.78 g)
(ii) bp 70° to 80°/27 mm (1.64 g)

Fraction (ii) contained the title ester which was characterised by its nmr (CDCl$_3$) and infrared (CHBr$_3$) spectra.

PREPARATION 5

(R,S) 1-Bromopropyl acetate

The preparation was analogous to Preparation 4 except that the following reagents were substituted and the mixture was allowed to react overnight at ca 5°.
Acetyl bromide (1.5 ml, 20 mmole)
Propionaldehyde (2.2 ml, 31 mmole)

The title ester (1.56 g) was isolated as a liquid bp 50° to 60°/20 mm characterised by its nmr (CDCl$_3$) spectrum.

EXAMPLE 1

(R and S)-1-Acetoxyethyl (6R,7R)-3-carbamoyloxymethyl-7-[(Z)-2-(fur-2-yl)-2-methoxyiminoacetamido]ceph-3-em-4-carboxylate Potassium carbonate (760 mg, 5.5 mmole) was added to a solution of (6R,7R)-3-carbamoyloxymethyl-7-[(Z)-2-(fur-2-yl)-2-methoxyiminoacetamido]ceph-3-em-4-carboxylic acid (4.57 g, 11 mmole) in N,N-dimethylformamide (25 ml) and the mixture was stirred at ca 20° for 25 minutes. 1-Bromoethyl acetate (1.8 g, 11 mmole) in N,N-dimethylformamide (5 ml) was added to the above solution and the reaction mixture was stirred for 40 minutes at ca 20°. The reaction mixture was worked up by pouring it into excess 2 N hydrochloric acid, followed by extraction with ethyl acetate (3 times). The combined organic extracts were washed with 2 N hydrochloric acid and saturated sodium bicarbonate solution, dried (magnesium sulphate) and evaporated in vacuo to yield a foam which was dissolved in ethyl acetate and precipitated from ether.

The resulting precipitate was filtered off and dried to give the title compound (780 mg).

The mother liquors were evaporated to a foam which was dissolved in ethyl acetate and precipitated from di-isopropyl ether to give a further crop of the title compound (1.21 g). This sample was dried in vacuo for 2 days at 22° in order to remove di-isopropyl ether. The physical constants of the second crop of the title compound are: mp ($M_{50}^2$) 72°; $[\alpha]_D$ +84° (c 0.87, DMSO); $\lambda_{max}$(EtOH)277 nm ($E_{1cm}^{1\%}$ 355, $\epsilon$18,120); microanalysis before drying in vacuo [Found; C, 46.6; H, 4.4; N. 10.95; S, 6.2; C$_{20}$H$_{22}$N$_4$O$_{10}$S (510.5) requires C, 47.1; H, 4.3; N, 10.9; S, 6.3%]. The infrared and nmr spectra are shown in Table 1 hereinafter.

EXAMPLE 2

(R and S)-1-Propionyloxyethyl (6R,7R)-3-carbamoyloxymethyl-7-[(Z)-2-(fur-2-yl)-2-methoxyiminoacetamido]ceph-3-em-4-carboxylate The method of preparation was analogous to that described in Example 1; 1-bromoethyl propionate (1.5 g, 8.3 mmole) was reacted with potassium (6R,7R)-3-carbamoyloxymethyl-7-[(Z)-2-(fur-2-yl)-2-methoxyiminoacetamido]-ceph-3-em-4-carboxylate (3.8 g, 8.3 mmole) in N,N-dimethylformamide (25 ml) at ca 22° for 30 minutes.

The reaction mixture was worked up as described in Example 1 to yield an oil which was dissolved in ethyl acetate and precipitated from ether (250 ml). The filtrate was evaporated to an oil which was dissolved in ethyl acetate and added dropwise to di-isopropyl ether. The precipitate was filtered and washed with di-isopropyl ether and dried to give the title compound (1.46 g, 2.8 mmole), mp ($M_{60}^2$) 81°; $[\alpha]_D$ +66° (c 1.2, DMSO); $\lambda_{max}$(EtOH)-276.5 nm ($E_{1cm}^{1\%}$ 362, ε18,085). The infrared and nmr data are shown in Table 1 hereinafter.

EXAMPLE 3

(R and S)-1-Butyryloxyethyl (6R,7R)-3-carbamoyloxymethyl-7-[(Z)-2-(fur-2-yl)-2-methoxyiminoacetamido]ceph-3-em-4-carboxylate A solution of potassium (6R,7R)-3-carbamoyloxymethyl-7-[(Z)-2-(fur-2-yl)-2-methoxyiminoacetamido]-ceph-3-em-4-carboxylate (1.025 g, 2.22 mmole) in N,N-dimethylformamide (12 ml) was treated with 1-bromoethyl butyrate (649 mg, 3.33 mmole) in N,N-dimethylformamide (2 ml) for 30 minutes at room temperature.

The reaction mixture was then worked up as described in Example 1 and after drying (over magnesium sulphate) and evaporation, a pale yellow foam (964 mg) was obtained. The foam was triturated with cyclohexane (80 ml) and the resultant solid was filtered off and washed with cyclohexane (2×20 ml) and dried in vacuo to give the title compound (711 mg) as an off-white solid; mp ($M_{51}^3$) 84°; $[\alpha]_D$ +36° (c 1.13, DMSO): $\lambda_{max}$ (EtOH)-276.5 nm ($E_{1cm}^{1\%}$ 350, ε18,850); [Found: C, 48.8; H, 5.0; N, 10.1; S, 5.5; $C_{22}H_{26}N_4O_{10}S$ (538.5) requires C, 49.1; H, 4.9; N, 10.4; S, 5.95%].

The infrared and nmr data are shown in Table 1 hereinafter.

EXAMPLE 4(a)

(R and S)-1-Isovaleryloxyethyl (6R,7R)-3-carbamoyloxymethyl-7-[(Z)-2-(fur-2-yl)-2-methoxyiminoacetamido]ceph-3-em-4-carboxylate and (R and S)-1-Isovaleryloxyethyl (4R,6R,7R)-3-carbamoyloxymethyl-7-[(Z)-2-(fur-2-yl)-2-methoxyiminoacetamido]ceph-2-em-4-carboxylate 1-Bromoethyl-3-methylbutyrate (2.38 g, 11.4 mmole) was added to a stirred solution of potassium (6R,7R)-3-carbamoyloxymethyl-7-[(Z)-2(fur-2-yl)-2-methoxyiminoacetamido]ceph-3-em-4-carboxylate (4.2 g, 9.1 mmole) in N,N-dimethylformamide (50 ml) at ca 22° for 35 minutes. The reaction mixture was then worked up in a similar manner to that described in Example 1 and the product (2.15 g) was precipitated from di-isopropyl ether. The nmr spectrum (DMSO-d6) indicated that the product was approximately a 1:1 mixture of the two title compounds.

(b) (R and S)-1-Isovaleryloxyethyl (1S,6R,7R)-3-carbamoyloxymethyl-7-[(Z)-2-(fur-2-yl)-2-methoxyiminoacetamido]ceph-3-em-4-carboxylate 1-oxide A solution of the mixture of esters produced in Example 4(a) (2.0 g) in dichloromethane (50 ml) was treated with m-chloroperbenzoic acid (1.0 g, 5.7 mmole) for 40 minutes at ca 22°.

The solvent was evaporated in vacuo and the residue was triturated with ether to give the title compound (1.8 g) as a solid, mp ($M_{150}^2$) 167.5°; $[\alpha]_D$ +52° (c 0.5, DMSO); [Found; C, 47.1; H, 4.7; N, 10.05; S, 5.8; $C_{23}H_{28}N_4O_{11}S$ (568.5) requires C, 48.6; H, 4.95; N, 9.85; S, 5.65%].

(c) (R and S)-1-Isovaleryloxyethyl (6R,7R)-3-carbamoyloxymethyl-7-[(Z)-2-(fur-2-yl)-2-methoxyiminoacetamido]ceph-3-em-4-carboxylate Potassium iodide (1.95 g, 11.7 mmole) and acetyl chloride (460 mg, 5.9 mmole) were added successively to a solution of (R and S)-1-isovaleryloxyethyl (1S,6R,7R)-3-carbamoyloxymethyl-7-[(Z)-2-(fur-2-yl)-2-methoxyiminoacetamido]ceph-3-em-4-carboxylate 1-oxide (1.67 g, 2.9 mmole) in N,N-dimethylformamide (50 ml).

The solution was stirred at ca 22° for 35 minutes and was then added dropwise to an aqueous solution of sodium metabisulphite. The precipitate was filtered off and washed with water and dried in vacuo over phosphorus pentoxide to give the title compound (1.19 g, 2.1 mmole) as a solid, mp ($M_{70}^2$) 92°; $[\alpha]_D$ +24° (c 0.9, DMSO); $\lambda_{max}$ (EtOH) 276 nm ($E_{1cm}^{1\%}$ 360, ε19,890); [Found C, 48.1; H, 4.95; N, 10.35; S, 6.0; $C_{23}H_{28}N_4O_{10}S$ (552.5) requires C, 49.9; H, 5.1; N, 10.1; S. 5.8%].

The infrared and nmr data are shown in Table 1 hereinafter.

EXAMPLE 5

(R and S)-1-Acetoxybutyl (6R,7R)-3-carbamoyloxymethyl-7-[(Z)-2-(fur-2-yl)-2-methoxyiminoacetamido]ceph-3-em-4-carboxylate Potassium (6R,7R)-3-carbamoyloxymethyl-7-[(Z)-2-(fur-2-yl)-2-methoxyiminoacetamido]ceph-3-em-4-carboxylate (1.850 g, 4 mmole) was added to a solution of 1-bromobutyl acetate (780 mg, 4 mmole) in purified N,N-dimethylformamide (10 ml) resulting in the formation of a brown solution and evolution of heat. After ca 10 minutes solid started separating out and after 20 minutes the reaction mixture was worked up by pouring it into 2 N hydrochloric acid (120 ml) to give a pale yellow solid which dissolved on addition of ethyl acetate (120 ml).

The organic layer was separated and washed with saturated aqueous sodium bicarbonate (120 ml) and brine (60 ml), dried over magnesium sulphate and evaporated to a pale yellow foam (1.378 g). Trituration of this foam with di-isopropyl ether (30 ml) gave a pale solid which was filtered off and washed with more di-isopropyl ether and dried in vacuo to give the title compound (1.261 g) as a cream powder, mp 59° to 68°; $[\alpha]_D^{21}$ +54.5° (c 1.0, DMSO); $\lambda_{max}$ (EtOH) 277 nm ($E_{1cm}^{1\%}$ 333, ε17,930); [Found: C, 50.1; H, 5.5; N, 9.4; S, 5.1; $C_{22}H_{26}N_4O_{10}S$ (538.5) requires C, 49.05; H, 4.85; N, 10.4; S, 5.95%]. The nmr and infrared data are shown in Table 1 hereinafter.

EXAMPLE 6

(R and S)-1-Acetoxypropyl (6R, 7R)-3-carbamoyloxymethyl-7-[(Z)-2-fur-2-yl)-2-methoxyiminoacetamido]ceph-3-em-4-carboxylate A solution of potassium (6R, 7R)-3-carbamoyloxymethyl-7-[(Z)-2-(fur-2-yl)-2-methoxyiminoacetamido]-ceph-3-em-4-carboxylate (3.7 g, 8 mmole) in N,N-dimethylformamide (50 ml) was stirred at ca 22° for 45 minutes with 1-bromopropyl acetate (1.45 g, 8 mmole). The workup was similar to that described in Example 5 except that the crude product was purified by precipitation from ethyl acetate solution using di-isopropyl ether to give on drying in vacuo the title compound (920 mg), mp ($M_{51}{}^2$) 81°; $[\alpha]_D + 69°$ (c 0.87 DMSO); $\lambda_{max}$ (EtOH) 277 nm ($E_{1\,cm}{}^{1\%}$349, $\epsilon$18,305); [Found; C, 48.15; H, 4.8; N, 10.45; S, 5.9; $C_{21}H_{24}N_4O_{10}S$ (524.5) requires C, 48.1; H, 4.6; N, 10.7; S, 6.1%]

The nmr and infrared data are shown in Table 1 hereinafter.

EXAMPLE 7

(R and S)-1-Acetoxyheptyl(6R,7R)-3-carbamoyloxymethyl-7-[(Z)-2-(fur-2-yl)-2-methoxyiminoacetamido]ceph-3-em-4-carboxylate Potassium carbonate (0.21 g) was added to a solution of (6R,7R)-3-carbamoyloxymethyl-7-[(Z)-2-(fur-2-yl)-2-methoxyiminoacetamido]ceph-3-em-4-carboxylic acid (1.27 g) in N,N-dimethylformamide (7 ml), with stirring, at 23°. Most of the potassium carbonate dissolved within 10 minutes, giving a dark solution. 1-Bromoheptyl acetate (0.72 g) was added as a solution in N,N-dimethylformamide (1.5 ml). Precipitation commenced after 15 minutes, and after 18 minutes the reaction mixture was poured into 2 N-hydrochloric acid (75 ml), giving a brown gum. This dissolved on addition of ethyl acetate (75 ml). The organic layer was separated, washed successively with 2 N-hydrochloric acid (75 ml) and saturated sodium bicarbonate solution (75 ml), and was dried (Mg SO$_4$) and evaporated in vacuo to give a brown glass (1.01g). Trituration of this material with petroleum ether (b.p. 40° to 60°-3×15 ml) gave a pale yellow solid which was filtered, washed with petroleum ether (40°-60°) and dried in vacuo to give the title compound as a pale yellow powder (0.75 g), m.p. 68° to 71° (decomp.); $[\alpha]_D{}^{22} + 46°$ (c 1.00, DMSO); $\lambda_{max}$ (EtOH) 276.5 nm ($\epsilon$18,154).

The nmr and infrared data are shown in Table 1 hereinafter.

EXAMPLE 8

1-Acetoxyethyl (6R,7R)-3-carbamoyloxymethyl-7-[(Z)-2-(fur-2-yl)-2-methoxyiminoacetamido]ceph-3-em-4-carboxylate (Isomer A)

A solution of (R and S)-2-Acetoxyethyl (6R,7R)-3-carbamoyloxymethyl-7-[(Z)-2-(fur-2-yl)-2-(methoxyiminoacetamido]ceph-3-em-4-carboxylate (ca. 1:1; ca. 1 g) in methanol (3 ml) was cooled to 0° and left overnight to give a crystalline deposit of Isomer A (300 mg) which was shown by nmr spectroscopy (DMSO-d$_6$) to contain essentially one isomer.

The mother liquors were evaporated to dryness in vacuo and the residue was dissolved in ethyl acetate and precipitated from petroleum (40°-60°). Nmr (DMSO-d$_6$) indicated that the precipitate consisted of a ca. 65:35 mixture of diastereoisomers B and A respectively.

EXAMPLE 9

Separation of the diastereoisomers of 1-acetoxyethyl(6R,7R)-3-carbamoyloxymethyl-7-[(Z)-2-(fur-2-yl)-2-methoxyiminoacetamido]ceph-3-em-4-carboxylate (Isomer A and Isomer B)

A solution of (R and S)-1-Acetoxyethyl-(6R,7R)-3-carbamoyloxymethyl-7-[(Z)-2-(fur-2-yl)-2-methoxyiminoacetamido]ceph-3-em-4-caboxylate (ca. 1:1; 5.0 g, 9.8 mmole) in methanol (7.5 ml) at ca. 25° was seeded with a sample of Isomer A (prepared as described in Example 8). The solution solidified and was refrigerated at 0° overnight. Filtration gave a solid (1.7 g) which on recrystallization from methanol (30 ml) afforded essentially pure Isomer A (1.28 g) (Fraction 1).

A second crop of crystals (110 mg. Fraction 2) was obtained from the mother-liquors. This was shown by nmr (DMSO-d$_6$) to contain a ca. 1:1-ratio of Isomer A to Isomer B.

The residual mother-liquors were evaporated in vacuo to dryness and the residual gum was taken up in ethyl acetate and refrigerated whereupon the solution solidified, so ethyl acetate was added to give a total volume of ca. 15 ml and the mixture was heated to reflux. A small portion of solid did not dissolve and so was filtered off (Fraction 3, 190 mg). Fraction 3 was shown by nmr spectroscopy (DMSO-d$_6$) to consist of essentially Isomer B.

The filtrate was refrigerated and slowly solidified. The resultant solid was filtered off and dried (Fraction 4, 410 mg). Fraction 4 consisted of essentially Isomer B (ca 80% pure) as shown by nmr spectroscopy (DMSO-d$_6$) and HPLC.

The mother liquor from the Fraction 4 separation was evaporated to dryness and the resultant solid triturated with ethyl acetate-ether. The solid obtained was filtered and dried (Fraction 5, 640 mg). Fraction 5 consisted of an approximately 70:30 mixture of Isomers B to A, as shown by nmr (DMSO-d$_6$).

Fraction 1 (Isomer A) and Fraction 4 (Isomer B) have the following physical properties:

Isomer A (Fraction 1): m.p. $[M]_{179}{}^2$ 191°, $[\alpha]_D + 53°$ (c 0.9, DMSO), $\lambda_{max}$ (EtOH) 277 nm ($E_{1\,cm}{}^{1\%}$ 414, $\epsilon$21,130), [Found: C, 46.95; H, 4.4; N, 10.9; S, 6.5, $C_{20}H_{22}N_4O_{10}S$ (510.5) requires C, 47.1; H, 4.3; N, 10.9; S, 6.3%]. HPLC indicated an isomer purity of ca 94%.

Isomer B (Fraction 4): m.p. $[M]_{113}{}^2$ 129°, $[\alpha]_D + 11°$ (c 1.2, DMSO), $\lambda_{max}$ (EtOH) 277 nm ($E_{1cm}{}^{1\%}$ 422, $\epsilon$22,700), [Found: C, 46.8; H, 4.5; N, 10.35; S, 5.9 $C_{20}H_{22}N_4O_{10}S$, 0.3 mole EtOAc (539.9) requires C, 47.45; H, 4.6; N, 10.4; S, 5.9%]. HPLC indicated an Isomer B purity of ca. 80%.

The nmr and infrared data for the two isomers are shown in Table 1 hereinafter.

TABLE 1
Physical Properties of the products of Examples 1 to 7 and 9

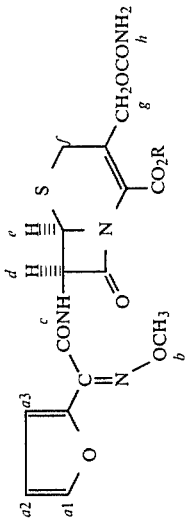

| Example No. | Solvent | τ (100MHz; J Hz) a1a2a3 | b | c | d | e | f | g | h | R | Assignment for R τ | Solvent | $HN_2$ + NH | β-lactam | CONH | $CO_2R$ | $OCONH_2$ |
|---|---|---|---|---|---|---|---|---|---|---|---|---|---|---|---|---|---|
| 1 | DMSO-d6 | 2.11(m) 3.2 to 3.4(m) | 6.08 | 0.20 (d9) | 4.06 (multi-plets) | 4.69 4.73 (d5) | 6.23 6.45 (J18) | 5.13 5.35 (J12) | 3.30 obscured by a2 and a3 | —CHOCCH₃ (i,O,k) / CH₃ (j) | i 2.96,3.06(m) j 8.49(d6) k 7.92 | $CHBr_3$ | 3540 3400 | 1780 | 1686 1520 | 1750 1730 | 1730 1584 |
| 2 | DMSO-d6 | 2.14(m) 3.2 to 3.4(m) | 6.09 | 0.22 (d8) | 4.10 (multi-plets) | 4.74 4.77 (d5) | 6.24 6.47 (J18) | 5.14 5.38 (J12) | 3.36 | —CHOCCH₂CH₃ / CH₃ | i 2.95,3.04(m) j 8.49(d6) k 7.60(q7) l 8.96(t7) | $CHBr_3$ | 3514 3380 | 1786 | 1686 1520 | 1750 1730 | 1730 1582 |
| 3 | DMSO-d6 | 2.16(m) 3.2 to 3.4(m) | 6.11 | 0.22 (d8) | 4.12 4.15 (dd 8,5) | 4.75 4.77 (d5) | 6.40 (s) | 5.16 5.39 (J12) | 3.38 | —CHOCCH₂CH₂CH₃ / CH₃ | i 2.99,3.06(q6) j 8.53 (d6) k 7.68 (t7) l 8.3 to 8.6(m) m 9.12 (t7) | Nujol | 3470 3370 3300 | 1790 | 1680 1534 | 1720 1730 | 1720 1592 |
| 4 | DMSO-d6 | 2.15(m) 3.2 to 3.4(m) | 6.10 | 0.21 (d8) | 4.14 (multi-plets) | 4.74 4.75 (d5) | 6.38 (s) | 5.16 5.38 5.16 5.41 (J12) | 3.38 | —CHOCCH(CH₃)₂ / CH₃ | i 3.05(m) j 8.50(d6) k 7.75(d6) l 7.94(m) m 9.07(d7) | $CHBr_3$ | 3500 3380 | 1790 | 1688 1522 | 1734 (strong) | 1730 1588 |
| 5 | DMSO-d6 | 2.17(m) 3.2 to 3.4(m) | 6.10 | 0.22 (d8) | 4.12 4.15 (dd 8,5) | 4.84 4.86 (d5) | 6.26 6.49 (J18) | 5.17 & 5.37 5.17 & 5.41 (J13) | 3.40 | —CHOCCH₂CH₃ / CH₃ | i 3.05 & 3.15(t6) j 7.94 k 8.20(m) l 8.3 to 8.8(m) m 9.09(t7) | $CHBr_3$ | 3510 3380 | 1790 | 1688 1522 | 1758 1734 | 1730 1588 |
| 6 | DMSO-d6 | 2.16(m) 3.2 to 3.4(m) | 6.10 | 0.22 (d8) | 4.12 4.14 (dd 8,5) | 4.74 4.76 (d5) | 6.28 6.49 (J18) | 5.16 & 5.38 5.16 & 5.42 (J13) | 3.38 | —CHOCCH₃ / CH₂CH₃ | i 3.12, 3.21(t6) j 7.93 k 8.17(m) l 9.07(t7) | $CHBr_3$ | 3520 3390 | 1788 | 1690 1520 | 1756 1732 | 1730 1584 |
| 7 | DMSO-d6 | 2.14(s) 3.2 to 3.4(m) | 6.06 | 0.20 (d8) | 4.10 (m) | 4.72 (d4) | 6.36 (s) | 5.15 5.36 (J12) | obscured by a2 and a3 | —CHOCCH₃ / $CH_2(CH_2)_4CH_3$ | i 3.08(m) j 8.20(m) k 8.4 to 8.9(m) l 9.11(broad s) m 7.91(s) | $CHBr_3$ | 3502 3370 | 1782 | 1690 1518 | 1750 1730 | 1730 |

TABLE 1-continued

Physical Properties of the products of Examples 1 to 7 and 9

[Structure shown:
$a^1, a^2, a^3$ - furan ring
CONH (c)
C=N-OCH$_3$ (b)
H (d), H (e)
β-lactam with S
CH$_2$OCONH$_2$ (g, h)
CO$_2$R]

| Example No. | Solvent | $\tau$ (100MHz, J Hz) | | | | | | | R | Assignment for R $\tau$ | Solvent | HN$_2$ + NH | β-lactam | CONH | CO$_2$R | OCONH$_2$ |
|---|---|---|---|---|---|---|---|---|---|---|---|---|---|---|---|---|
| | | a$_1$a$_2$a$_3$ | b | c | d | e | f | g h | | | | | | | | |
| 9 Isomer A | DMSO-d6 | 2.16(d) 3.37 (dd 3,2) 3.30 (d3) | 6.10 | 0.21 (d8) | 4.12 (dd 8,5) | 4.74 (d5) | 6.40 ABq | 5.16 5.39 (J12) | 3.40 | −CHOCCH$_3$ (i, O=k) CH$_3$ (j) | i 3.08(q5) j 8.51(d5) k 7.94 | Nujol | 3504 3440 to 3100 | 1780 | 1661 1521 | 1750 | 1710 |
| 9 Isomer B | DMSO-d6 | 2.17(d2) 3.38 (dd 3,2) 3.29 (d3) | 6.09 | 0.22 (d8) | 4.15 (dd 8,5) | 4.76 (d5) | 6.39 ABq | 5.15 5.40 (J12) | 3.40 | −CHOC−CH$_3$ (i, O=, k) CH$_3$ (j) | i 2.99(q5) j 8.50(d5) k 7.94 | Nujol | 3420 3310 3290 3220 | 1778 | 1661 1528 | 1712 | 1710 |

EXAMPLE A

Tablet

| Composition: | |
|---|---|
| 1-Acetoxyethyl (6R,7R)-3-carbamoyloxymethyl-7-[(Z)-2-(fur-2-yl)-2-methoxyiminoacetamido]ceph-3-em-4-carboxylate (micronised) | 326.0 mg |
| Sodium starch glycolate (Primojel) | 8.0 mg |
| Microcrystalline cellulose (Avicel PH101) | 64.0 mg |
| Magnesium stearate | 2.0 mg |
| Total weight | 400.0 mg |

Method of preparation

The magnesium stearate was blended with the active ingredient and tablet slugs/were prepared by direct compression. The slugs were broken down through 12 mesh, 16 mesh and 20 mesh consecutively and the granules were blended with the sodium starch glycolate and microcrystalline cellulose. The blend was compressed on concave punches to a tablet weight of 400 mg. The tablets may be film coated by the aqueous or organic solvent method using cellulose derivatives with plasticisers and colouring matter. As an alternative to the preliminary slugging stage, the active ingredient may be densified by roller compaction.

EXAMPLE B

Powder for oral suspension (in sachet)

| Composition (per sachet) | |
|---|---|
| 1-Acetoxyethyl (6R,7R)-3-carbamoyloxymethyl-7-[(Z)-2-(fur-2-yl)-2-methoxyiminoacetamido]ceph-3-em-4-carboxylate (milled) | 326.0 mg |
| Lecithin | 25mg |
| Sodium carboxymethyl cellulose (low viscosity) | 90mg |
| Spray-dried orange flavour | 150mg |
| Caster sugar | 2.2g |

Method of preparation

The lecithin was dissolved in chloroform and triturated with the active ingredient (previously milled using a fluid energy mill). The chloroform was allowed to evaporate and the resultant solid powdered. It was then blended intimately with the sodium carboxymethyl cellulose and the flavour. This blend was then further blended with the caster sugar adding the latter in two stages. It was intended that the correct weight should be filled into a sachet of suitable laminated foil and sealed by heat. The powder would be used by constituting with about 15 mls water shortly before administration.

We claim:

1. A cephalosporin antibiotic of the sym form having a formula

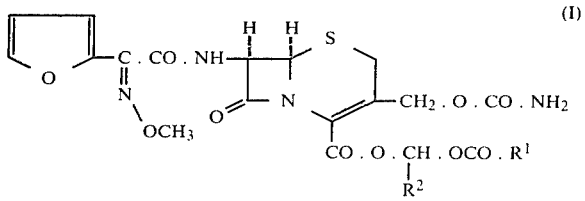

(wherein $R^1$ is a primary or secondary alkyl group containing 1 to 4 carbon atoms and $R^2$ is a primary or secondary alkyl group containing 1 to 6 carbon atoms provided that at least one of the groups $R^1$ and $R^2$ is methyl).

2. A compound as claimed in claim 1 wherein $R^1$ is a methyl group and $R^2$ is an alkyl group containing 2 to 4 carbon atoms.

3. A compound as claimed in claim 1 wherein $R^2$ is a methyl group and $R^1$ is a primary or secondary alkyl group containing 1 to 4 carbon atoms.

4. The compound claimed in claim 1 which is 1-acetoxyethyl (6R,7R)-3-carbamoyloxymethyl-7-[(Z)-2-(fur-2-yl)-2-methoxyiminoacetamido]ceph-3-em-4-carboxyylate.

5. The compound of claimed in claim 1 which is 1-propionyloxyethyl (6R,7R)-3-carbamoyloxymethyl-7-[(Z)-2-(fur-2-yl)-2-methoxyiminoacetamido]ceph-3-em-4-carboxylate.

6. The compound claimed in claim 1 which is 1-butyryloxyethyl (6R,7R)-3-carbamoyloxymethyl-7-[(Z)-2-(fur-2-yl)-2-methoxyiminoacetamido]ceph-3-em-4-carboxylate.

7. The compound claimed in claim 1 which is 1-isovaleryloxyethyl (6R,7R)-3-carbamoyloxymethyl-7-[(Z)-2-(fur-2-yl)-2-methoxyiminoacetamido]ceph-3-em-4-carboxylate.

8. The compound claimed in claim 1 which is 1-acetoxyheptyl (6R,7R)-3-carbamoyloxymethyl-7-[(Z)-2-(fur-2-yl)-2-methoxyiminoacetamido]ceph-3-em-4-carboxylate.

9. The compound claimed in claim 1 which is 1-acetoxybutyl (6R,7R)-3-carbamoyloxymethyl-7-[(Z)-2-(fur-2-yl)-2-methoxyiminoacetamido]ceph-3-em-4-carboxylate.

10. The compound claimed in claim 1 which is 1-acetoxypropyl (6R,7R)-3-carbamoyloxymethyl-7-[(Z)-2-(fur-2-yl)-2-methoxyiminoacetamido]ceph-3-em-4-carboxylate.

11. A diastereosiomer of a compound as claimed in claim 1.

* * * * *

UNITED STATES PATENT AND TRADEMARK OFFICE

CERTIFICATE EXTENDING PATENT TERM
UNDER 35 U.S.C. 156

Patent No.    : 4,267,320

Dated         : May 12, 1981

Inventor(s)   : Michael Gregson et al

Patent Owner  : Glaxo Operations UK Limited

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

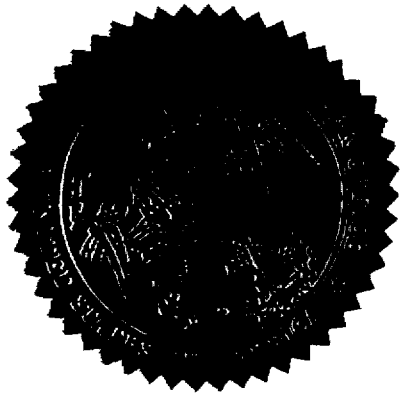

I have caused the seal of the Patent and Trademark Office to be affixed this 25th day of April 1990.

Harry F. Manbeck, Jr.
Assistant Secretary and Commissioner of Patents and Trademarks